US006318619B1

(12) United States Patent
Lee

(10) Patent No.: US 6,318,619 B1
(45) Date of Patent: Nov. 20, 2001

(54) AUTOMATIC CLIP DRIVER

(76) Inventor: Yong-woo Lee, 436 Gahyun-ri, Tongin-myun, Gimpo, Kyunggi-do 415-860 (KR)

( * ) Notice: Subject to any disclaimer, the term of this patent is extended or adjusted under 35 U.S.C. 154(b) by 0 days.

(21) Appl. No.: 09/851,777

(22) Filed: May 9, 2001

(30) Foreign Application Priority Data

Mar. 29, 2001 (KR) ............................................ 2001-16441

(51) Int. Cl.[7] ..................................................... A61B 17/00

(52) U.S. Cl. ............................ 227/134; 227/19; 227/120; 227/127; 29/243.56

(58) Field of Search ............................. 227/19, 134, 127, 227/120, 123; 29/243.56, 809

(56) References Cited

U.S. PATENT DOCUMENTS 4,996,755 * 3/1991 Sato .................................. 29/243.56
5,119,553 * 6/1992 Sato .................................. 29/243.56
5,152,423 * 10/1992 Tseng ................................ 29/243.56
5,890,642 * 4/1999 Sato ..................................... 227/134
6,067,706 * 5/2000 Sato ....................................... 29/809

* cited by examiner

*Primary Examiner*—Scott A. Smith
(74) *Attorney, Agent, or Firm*—Darby & Darby

(57) ABSTRACT

Disclosed is an automatic clip driver including an upper case having a cover coupling section formed with a clip insertion hole, and a knob mounting section having a knob slide slot for receiving a pushing knob to be longitudinally slidable, a lower case coupled to the upper case, an opening/closing cover hingably coupled to the upper case to selectively open the cover coupling section, a clip pushing member interposed between the upper and lower cases and adapted to forwardly urge clips received in a clip receiving space defined between the upper and lower cases, a first elastic member connected between the opening/closing cover and the clip pushing member and adapted to forwardly or rearwardly urge the clip pushing member in accordance with an opening or closing movement of the opening/closing cover, and a second elastic member connected between the pushing knob and the upper case and adapted to urge the pushing knob to be always positioned at a rear end of the knob slide slot.

3 Claims, 6 Drawing Sheets

AUTOMATIC CLIP DRIVER

BACKGROUND OF THE INVENTION

1. Field of the Invention

The present invention relates to an automatic clip driver, and more particularly to an automatic clip driver capable of conveniently and continuously conducting a document binding process by use of a clip at any posture (orientation or position) thereof.

2. Description of the Related Art

FIG. 1 illustrated a conventional clip driver for binding sheets of paper such as documents or the like by use of a clip. Referring to FIG. 1, a longitudinally-extending guide opening 1 is provided at the top wall of a casing 6. A pushing knob 5 is mounted to the top wall of the casing 6 in such a fashion that it slides longitudinally along the guide opening 1. The pushing knob 5 is provided at opposite side surfaces thereof with guide grooves 5' respectively engaged with opposite longitudinal edges 1' of the guide opening 1. A clip insertion slot 3 is formed at the rear end of the casing 6 in order to allow clips to be inserted into the interior of the casing 6. In order to use the clip driver having the above mentioned structure, the pushing knob 5 is first moved to the rear end of the guide opening 1 under the condition in which clips are received in the interior of the casing 6. Thereafter, the casing 6 is inclined in such a fashion that its rear end is raised, thereby causing the clips to move toward the front end of the casing where a document insertion inlet is formed. A Document is then inserted into the document insertion inlet. In this state, the pushing knob is moved toward the document insertion inlet to force the foremost clip to grasp the document. Thus, the document is bound by the clip.

However, the conventional clip driver having the above mentioned structure is inconvenient in use in that it requires a rearward movement of the pushing knob and a raising of the rear end of the casing for its use. In particular, where a repeated binding task is required, this cannot be easily carried. Furthermore, an increased binding time is involved in this case.

In addition, the conventional clip driver has a degraded appearance in that the clip insertion slot is externally exposed.

SUMMARY OF THE INVENTION

The present invention has been made in view of the above mentioned problems, and an object of the invention is to provide an automatic clip driver in which when an external force applied to a pushing knob is released after the foremost one of clips received in the clip driver is used to bind a document, one of the clips is automatically positioned at the front of the pushing knob, so that the document binding process can be conveniently and continuously conducted at any posture (orientation or position) of the clip driver.

In accordance with the present invention, this object is accomplished by providing an automatic clip driver comprising: an upper case having a downwardly-opened rectangular box shape, the upper case including a cover coupling section formed with a longitudinally-extending spring receiving slot and a clip insertion hole arranged at the rear of the spring receiving slot, and a knob mounting section arranged at the front of the cover coupling section while being integral with the cover coupling section, the knob mounting section having a knob slide slot for receiving a pushing knob while allowing the pushing knob to be longitudinally slidable, and a pair of guide rails respectively arranged at opposite side surfaces of the knob mounting section and adapted to guide the sliding movement of the pushing knob; a lower case coupled to the upper case while being mated with the upper case, the lower case being mounted with a pair of V-shaped plate springs at a front end thereof; an opening/closing cover hingably coupled to a rear end of the upper case to selectively open the cover coupling section of the upper case; the pushing knob received in the knob slide slot of the knob mounting section to be slidable along the knob slide slot; a clip pushing member interposed between the upper and lower cases, the clip pushing member being in contact with the guide rails of the upper case to be longitudinally slidable along the guide rails and serving to forwardly urge clips received in a clip receiving space defined between the upper and lower cases; a first elastic member connected between the opening/closing cover and the clip pushing member and adapted to forwardly or rearwardly urge the clip pushing member in accordance with an opening or closing movement of the opening/closing cover; and a second elastic member connected between the pushing knob and the upper case and adapted to urge the pushing knob to be always positioned at a rear end of the knob slide slot.

Preferably, the first elastic member comprises a tension coil spring connected at one end thereof to a fixing piece formed on an inner surface of the opening/closing cover at a front portion of the opening/closing cover while being connected at the other end thereof to a fixing piece formed on a lower surface of the clip pushing member at a front portion of the clip pushing member. The tension coil spring serves to rearwardly move the clip pushing member when the opening/closing cover is opened while being bent when the opening/closing cover is closed, so that it comes into contact with a rear end of the clip pushing member, thereby urging the clip pushing member to slide forwardly.

Preferably, the automatic clip driver further comprises engagement hooks extending downwardly from opposite side walls of the upper case, respectively, and engagement grooves formed at the lower case and engaged with the engagement hooks, respectively, to couple the upper and lower cases to each other.

BRIEF DESCRIPTION OF THE DRAWINGS

The above objects, and other features and advantages of the present invention will become more apparent after a reading of the following detailed description when taken in conjunction with the drawings, in which.

Figure 5:
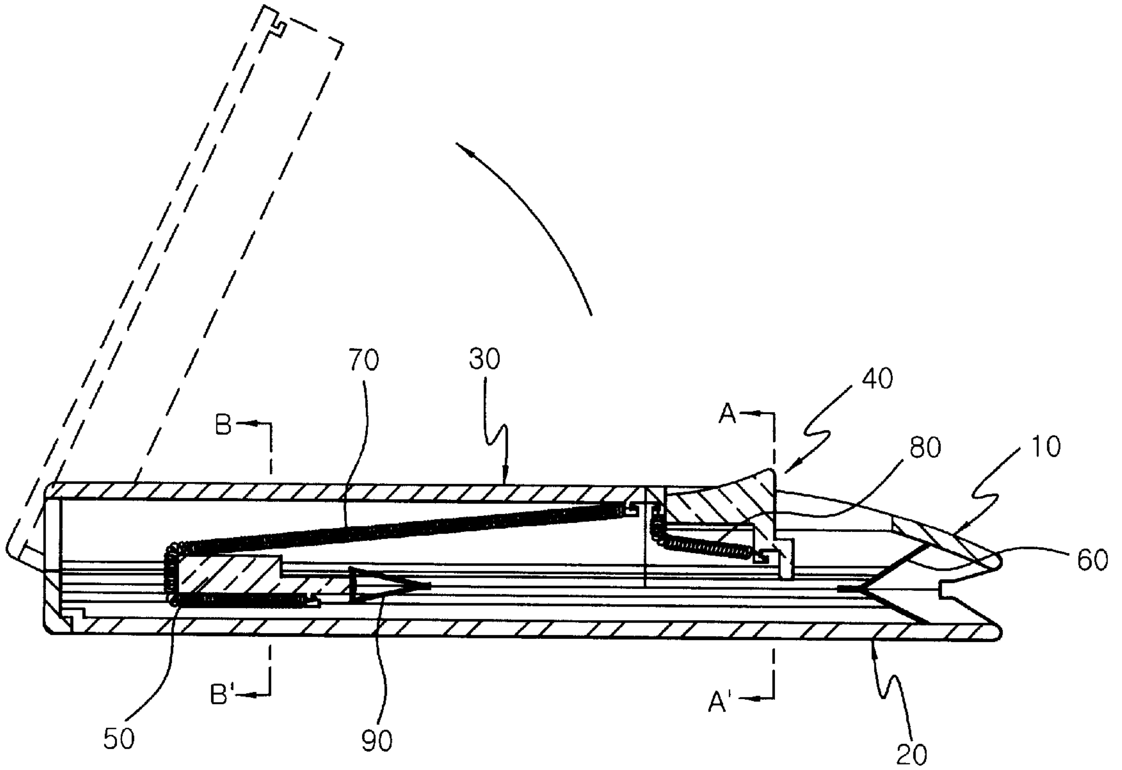
FIG. 5 is a sectional view illustrating one operation of the automatic clip driver according to the embodiment of the present invention.
Figure 7:
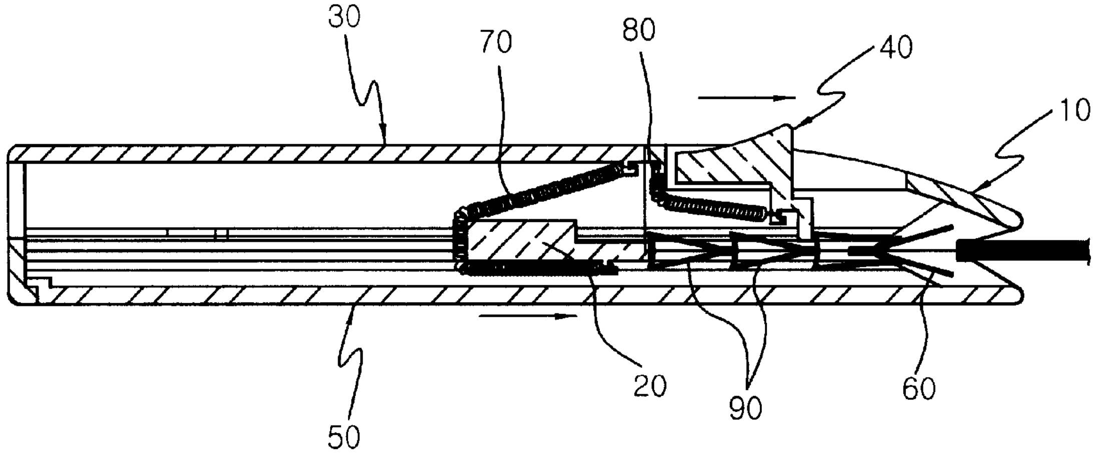

FIG. *6a* is a cross-sectional view taken along the line A–A' of FIG. 5;

FIG. *6b* is a cross-sectional view taken along the line B–B' of FIG. 5; and FIG. 7 is a sectional view illustrating another operation of the automatic clip driver according to the embodiment of the present invention.

DESCRIPTION OF THE PREFERRED EMBODIMENTS

Figure 1:
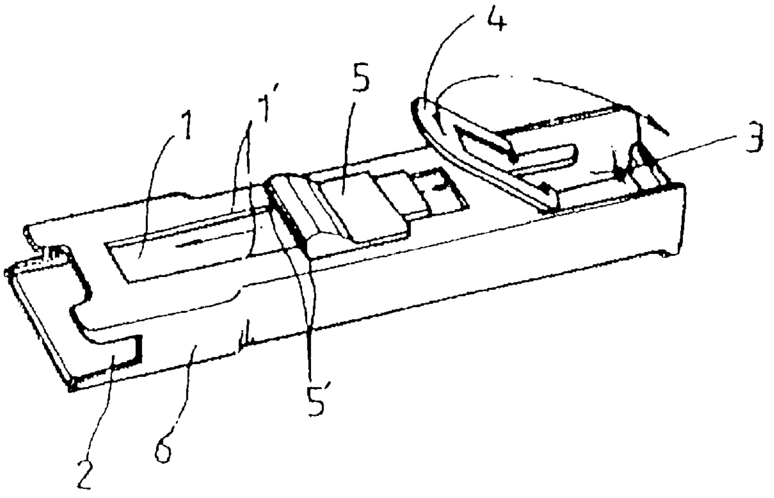
FIG. 1 Prior Art
FIG. 1 is a perspective view illustrating a conventional clip driver.
Figure 2:
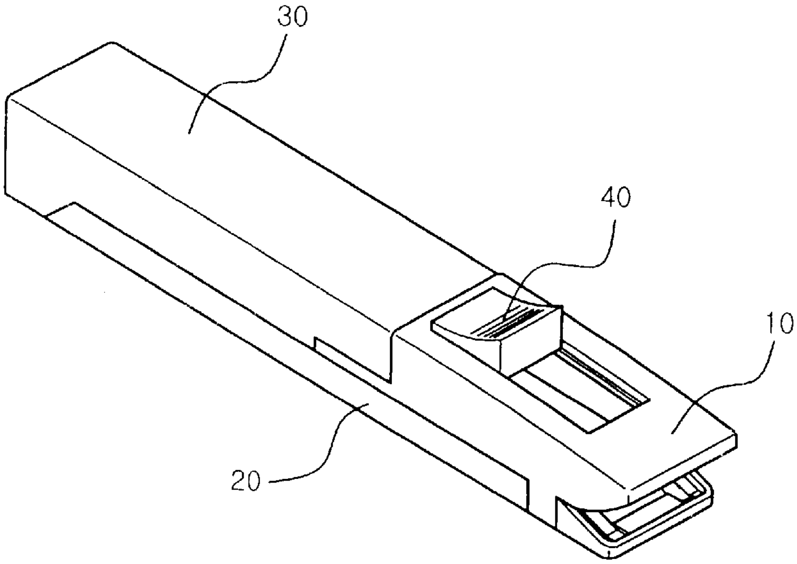
FIG. 2 is a perspective view illustrating an automatic clip driver according to an embodiment of the present invention.

Referring to FIG. 2, an automatic clip driver according to an embodiment of the present invention is illustrated. As shown in FIG. 2, the automatic clip driver includes an upper case 10, a lower case 20 coupled at an upper end thereof to a lower end of the upper case 10, an opening/closing cover 30 hingably coupled to the rear end of the upper case 20, and a pushing knob 40 mounted to the upper case 10 in such a fashion that it is longitudinally slidable in the front part of a clip receiving space defined between the upper and lower cases 10 and 20.

Figure 3:
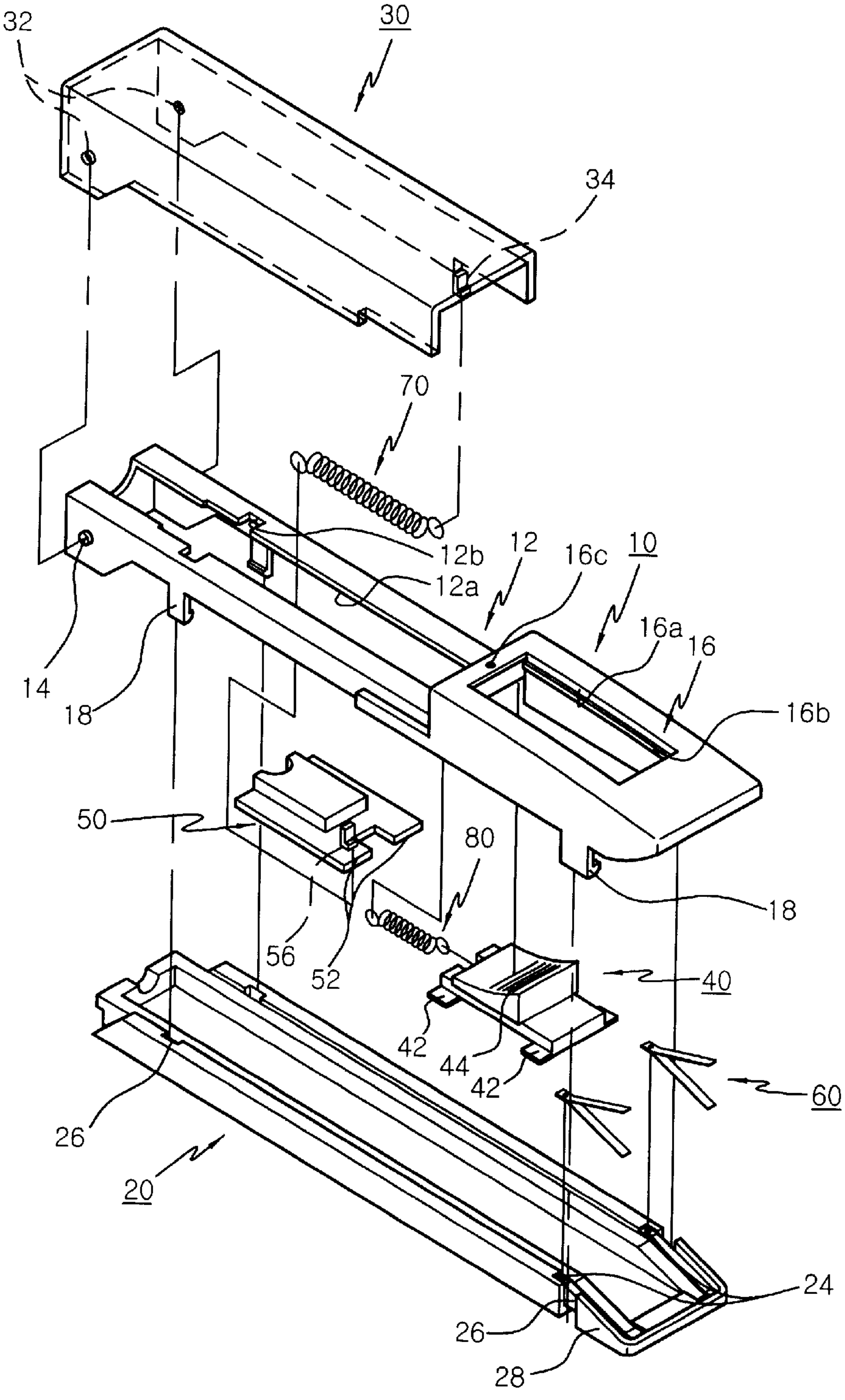
FIG. 3 is an exploded perspective view illustrating the automatic clip driver according to the embodiment of the present invention.
Figure 4:
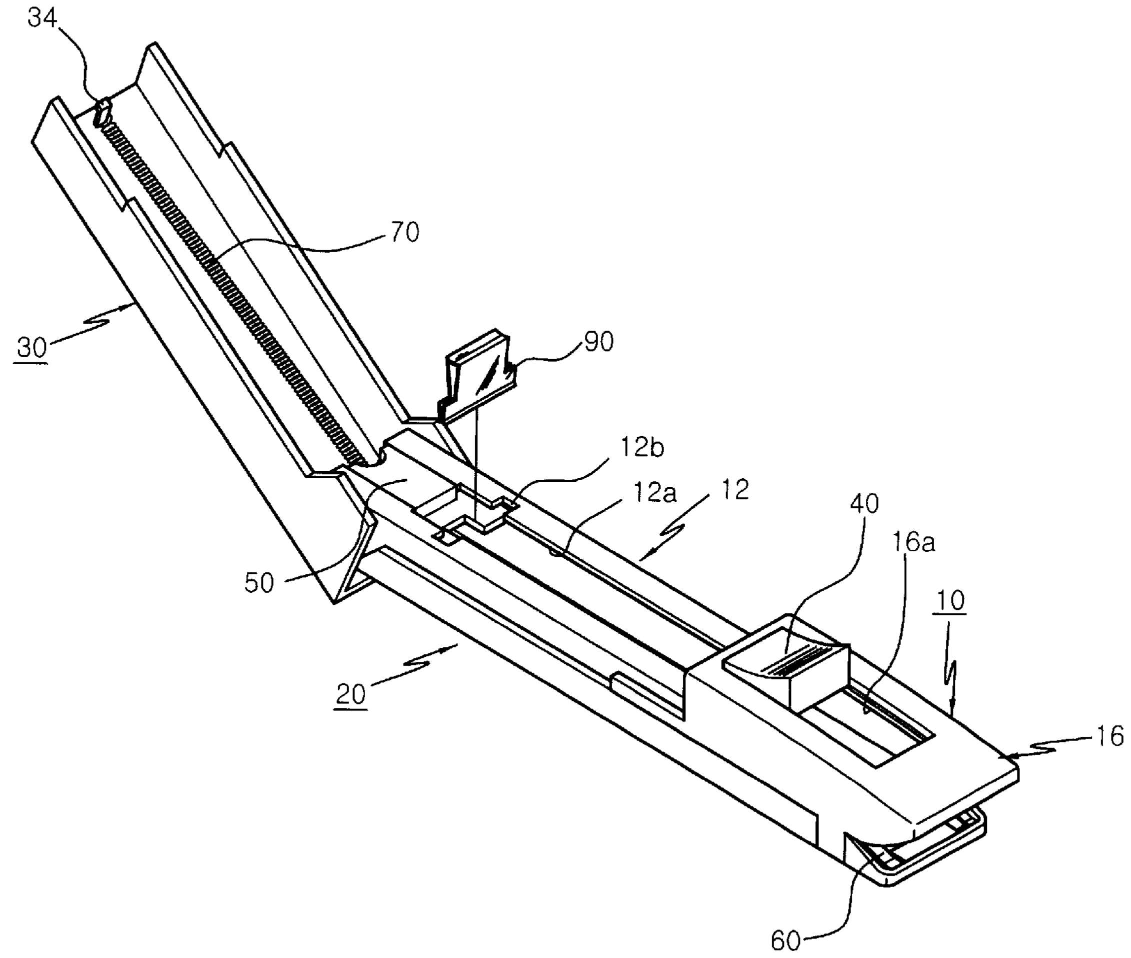
FIG. 4 is a perspective view illustrating a using condition of the automatic clip driver according to the embodiment of the present invention.

Referring to FIG. 3, the automatic clip driver also includes a clip pushing member 50 interposed between the upper and lower cases 10 and 20 in such a fashion that it is longitudinally slidable, and a pair of V-shaped plate springs 60 mounted to the lower case 20 at a document insertion inlet defined by respective front ends of the upper and lower cases 10 and 20. The automatic clip driver further includes a first elastic member 70 connected between the opening/closing cover 30 and the clip pushing member 50, and a second elastic member 80 connected between the pushing knob 40 and the upper case 10.

Figure 6A:
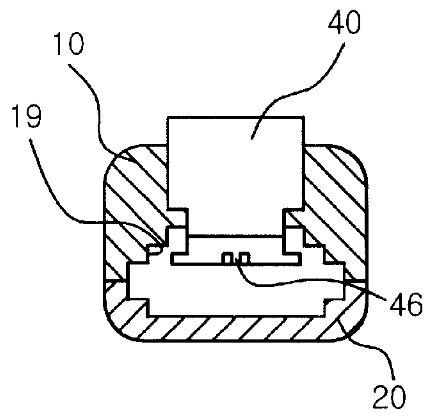
Figure 6B:
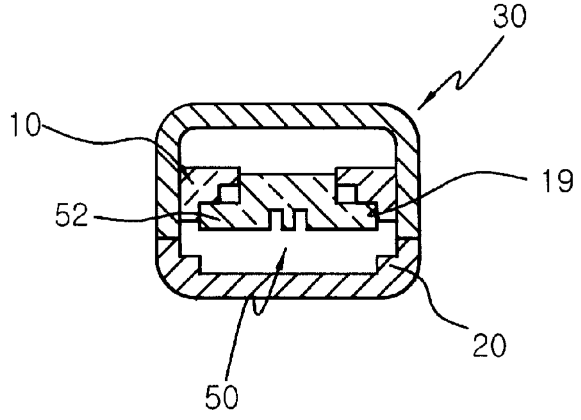

The upper case 10 has a body having a downwardly-opened rectangular box shape. The body of the upper case 10 is divided into a cover coupling section 12, and a knob mounting section 16 integral with the cover coupling section 12. The cover coupling section 12 has a longitudinally-extending spring receiving slot 12*a*, and a clip insertion hole 12*b* arranged at the rear of the spring receiving slot 12*a*. The knob mounting section 16 has a knob slide slot 16*a* for receiving the pushing knob 40 in such a fashion that the pushing knob 40 is longitudinally slidable along the knob slide slot 16*a*. The knob mounting section 16 also has a pair of guide rails 16*b* arranged at opposite side surfaces of the knob mounting section 16 and adapted to guide the sliding movement of the pushing knob 40. The knob mounting section 16 is also provided at its rear end with a fixing piece 16*c* for fixing one end of the second elastic member 80 thereto. A pair of engagement hooks 18 extend downwardly from opposite side walls of the knob mounting section 16 at the front portion of the knob mounting section 16, respectively. In similar, a pair of engagement hooks, which are denoted by the reference numeral 18, extend downwardly from opposite side walls of the cover coupling section 12 at the central portion of the cover coupling section 12, respectively. As shown in FIGS. 6*a* and 6*b*, the upper case 10 also includes a pair of guide rails 19 extending longitudinally along the side walls of the cover coupling section 12 and knob mounting section 16 at the lower ends of those sections 12 and 16, respectively. The guide rails 19 come into contact with ribs 52 respectively protruded from opposite side surfaces of the clip pushing member 50, thereby guiding the clip pushing member 50.

The lower case 20 has an upwardly-opened rectangular box shape. This lower case 20 is provided at its front end with a pair of spring fitting grooves 24 in which the plate springs 60 are fitted, respectively. The lower case 20 also has engagement grooves 26 respectively arranged at positions corresponding to the engagement hooks 18 of the upper case 10 and adapted to engage with those engagement hooks 18 so that the upper case 10 is coupled to the lower case 20. An inclined document guide 28 is also formed at the front of the lower case 20. This inclined document guide 28 defines the document insertion inlet with an inclined document guide formed at the upper case 10 in a similar fashion.

The opening/closing cover 30 has a downwardly-opened rectangular box shape. The opening/closing cover 30 has a pair of pin holes 32 respectively formed at opposite inner side surfaces of the opening/closing cover 30 and adapted to receive hinge pins 14 protruded from the opposite side surfaces of the cover coupling section 12 at the rear end of the cover coupling section 12. Thus, the opening/closing cover 30 is hingably coupled to the cover coupling section 12. A fixing piece 34 is formed at the inner surface of the opening/closing cover 30 near the front end of the opening/closing cover 30. The fixing piece 34 serves to fix one end of the first elastic member 70 thereto.

The pushing knob 40 includes a knob body having a rectangular cross-sectional shape. A plurality of ribs 42 are protruded from opposite side surfaces of the knob body at front and rear ends of the body, respectively. The ribs 42 are seated on the guide rails 16*b* of the knob mounting section 16 while allowing the pushing knob 40 to slide along the guide rails 16*b*. A fixing piece 46 is also provided at the lower surface of the knob body to fix the other end of the second elastic member 80 thereto. A finger contact section 44 is protruded from the upper surface of the knob body. The finger contact section 44 is adapted to receive an external force for sliding the pushing knob 40. In order to allow the user to easily manipulate the pushing knob 40, the finger contact section 44 has a taper shape having a cross-section gradually reduced as it extends from its front end to its rear end. The finger contact section 44 is also provided at its upper surface with anti-slip grooves.

The clip pushing member 50 has a substantially rectangular plate structure. As mentioned above, this clip pushing member 50 is interposed between the upper and lower cases 10 and 20, and formed with the ribs 52 slidably contacting the guide rails 19 of the upper case 10. The clip pushing member 50 is also provided at the front end thereof with a fixing piece 56 for fixing the other end of the first elastic member 70 thereto.

In the illustrated embodiment, the first elastic member 70 comprises a tension coil spring. This first elastic member 70 is connected between the fixing piece 34 of the opening/closing member 30 and the fixing piece 56 of the clip pushing member 50. In similar, the second elastic member 80 comprises a tension coil spring. This second elastic member 80 is connected between the fixing piece 46 arranged at the lower surface of the pushing knob 40 and the fixing piece 16*c* of the knob mounting section 16. By virtue of the second elastic member 80, the pushing knob 40 is always urged in a rearward direction.

The engagement hooks 18 provided at the upper case 10 are engaged with the engagement grooves 26 respectively provided at positions, corresponding to the engagement hooks 18, on the lower case 20, so that the upper and lower cases 10 and 20 are firmly coupled together without using any separate coupling means. In the illustrated case, the engagement hooks 18 are formed at the front portion of the knob mounting section 16 and the central portion of the cover coupling section 12, respectively. The engagement grooves 26 corresponding to the engagement hooks 18 of the knob mounting section 16 are formed at the side surfaces of the lower case 20 whereas the engagement grooves 26 corresponding to the engagement hooks 18 of the cover coupling section 12 are formed at the upper surface of the lower case 20. However, the numbers and positions of the engagement hooks and engagement grooves 26 may be varied without being limited to those described above.

Now, the operation of the automatic clip driver having the above mentioned configuration according to the present invention will be described.

In order to assemble the elements of the automatic clip driver, the plate springs 60 are first fitted in the spring fitting grooves 24 formed at the document guide 28 of the lower case 20, respectively. Also, one end of the first elastic member 70 is connected to the fixing piece 57 of the clip pushing member 50. The pushing knob 40 is also seated on the guide rails 16*b* of the knob mounting section 16 in the upper case 10. Thereafter, the second elastic member 80 is connected between the pushing knob 40 and the fixing piece 16*c* of the knob mounting section 16. In this state, the upper and lower cases 10 and 20 are coupled to each other in such a fashion that the clip pushing member 50 come into contact with the guide rails 19 of the upper case 10 so that its slide movement can be guided by the guide rails ribs 52. The other end of the first elastic member 70, which is connected to the clip pushing member 50 at one end thereof, is then connected to the opening/closing cover 30 which is, in turn, hingably coupled to the hinge pins 14 of the upper case 10. Thus, the assembling process for the automatic clip driver is completed. Of course, the assembling process is limited to the above mentioned assembling order and method.

When the opening/closing cover 30 is rotated in a counterclockwise direction indicated by an arrow in FIG. 5 after completion of the assembling process, the upper case 10 of the clip driver is opened. In accordance with the counterclockwise rotation of the opening/closing cover 30, an external force is applied to the first elastic member 70, thereby causing the clip pushing member 50 to be pulled in a rearward direction, that is, toward the rear end of the clip driver. In this state, the user can loads a plurality of clips 90 in the clip receiving space by inserting those clips one by one into the clip insertion hole 12*b*. After completion of the loading of clips, the opening/closing cover 30 is rotated in a clockwise direction so that it closes the upper case 10, as shown in FIG. 7. In accordance with the clockwise rotation of the opening/closing cover 30, the first elastic member 70 is bent at its portion contacting the rear end of the clip pushing member 50 while forwardly urging the clip pushing member 50. As a result, the clips 90 received in the clip receiving space are forwardly urged. By virtue of the urging force of the first elastic member 70, one clip is always automatically positioned at the front of the pushing knob 40.

When the user forwardly pushes the pushing knob 40, which is in contact with the rear end of the knob slide slot 16*a* by virtue of the urging force of the second elastic member 80, as shown in FIG. 7, the front end of the pushing knob 40 comes into contact with the rear end of the foremost clip 90 while being downwardly and forwardly moved. As a result, the pushing force is transmitted to the clip 90 which is, in turn, forwardly moved. Accordingly, the clip 90 comes into contact with the plate springs 60, and is then discharged into the document insertion inlet while being opened at its front end. Thus, the clip 90 grasps a document inserted into the document insertion inlet, so that the binding of the document is achieved.

When the external force applied to the pushing knob 40 is then released, the pushing knob is returned to its original position by virtue of the urging force of the second elastic member 80. At this time, one clip is automatically positioned at the front of the pushing knob 40 by virtue of the urging force of the first elastic member 70. Accordingly, the binding of documents can be easily, rapidly, and continuously conducted by repeating the above mentioned operation.

As apparent from the above description, in accordance with the automatic clip driver of the present invention, one of clips received in the clip driver is always automatically positioned at the front of the pushing knob by virtue of the urging force of the first elastic member. Accordingly, it is possible to repeatedly conduct the document binding process in a rapid and convenient fashion without any requirement to incline the clip driver. Accordingly, the automatic clip driver provides effects of a reduction in binding time and a convenience.

The automatic clip driver of the present invention also provides a good appearance in that the clip insertion hole is not externally exposed. In addition, this automatic clip driver is advantageous in that it is unnecessary to use any coupling means for coupling the upper and lower cases because the coupling of the upper and lower cases is achieved by the engagement hooks.

What is claimed is:

1. An automatic clip driver comprising:

an upper case having a downwardly-opened rectangular box shape, the upper case including a cover coupling section formed with a longitudinally-extending spring receiving slot and a clip insertion hole arranged at the rear of the spring receiving slot, and a knob mounting section arranged at the front of the cover coupling section while being integral with the cover coupling section, the knob mounting section having a knob slide slot for receiving a pushing knob while allowing the pushing knob to be longitudinally slidable, and a pair of guide rails respectively arranged at opposite side surfaces of the knob mounting section and adapted to guide the sliding movement of the pushing knob;

a lower case coupled to the upper case while being mated with the upper case, the lower case being mounted with a pair of V-shaped plate springs at a front end thereof;

an opening/closing cover hingably coupled to a rear end of the upper case to selectively open the cover coupling section of the upper case;

the pushing knob received in the knob slide slot of the knob mounting section to be slidable along the knob slide slot;

a clip pushing member interposed between the upper and lower cases, the clip pushing member being in contact with the guide rails of the upper case to be longitudinally slidable along the guide rails and serving to forwardly urge clips received in a clip receiving space defined between the upper and lower cases;

a first elastic member connected between the opening/closing cover and the clip pushing member and adapted to forwardly or rearwardly urge the clip pushing member in accordance with an opening or closing movement of the opening/closing cover; and a second elastic member connected between the pushing knob and the upper case and adapted to urge the pushing knob to be always positioned at a rear end of the knob slide slot.

2. The automatic clip driver according to claim 1, wherein the first elastic member comprises a tension coil spring connected at one end thereof to a fixing piece formed on an inner surface of the opening/closing cover at a front portion of the opening/closing cover while being connected at the other end thereof to a fixing piece formed on a lower surface of the clip pushing member at a front portion of the clip pushing member, the tension coil spring serving to rearwardly move the clip pushing member when the opening/closing cover is opened while being bent when the opening/closing cover is closed, so that it comes into contact with a rear end of the clip pushing member, thereby urging the clip pushing member to slide forwardly.

3. The automatic clip driver according to claim 1, further comprising:

engagement hooks extending downwardly from opposite side walls of the upper case, respectively; and engagement grooves formed at the lower case and engaged with the engagement hooks, respectively, to couple the upper and lower cases to each other.

* * * * *